United States Patent [19]

Epstein et al.

[11] 4,108,950

[45] Aug. 22, 1978

[54] PROCESS FOR PREPARING ORGANOPHOSPHORUS AND ORGANOPHOSPHONO FLUORINES

[75] Inventors: Joseph Epstein, Baltimore; George T. Davis, Bel Air, both of Md.

[73] Assignee: The United States of America as represented by the Secretary of the Army, Washington, D.C.

[21] Appl. No.: 792,427

[22] Filed: Apr. 29, 1977

[51] Int. Cl.² .......................... C07F 9/14; A01N 9/36
[52] U.S. Cl. ................................ 260/986; 260/543 F; 424/40
[58] Field of Search ............. 260/986, 960, 694, 543 F

[56] References Cited

FOREIGN PATENT DOCUMENTS 1,464,472 11/1966 France ...................................... 260/986
692,774 6/1953 United Kingdom ................. 260/543 F

*Primary Examiner*—Anton H. Sutto
*Attorney, Agent, or Firm*—Nathan Edelberg; Kenneth P. Van Wyck

[57] ABSTRACT

A method of preparing anticholinesterase organophosphoro and organophosphono-fluoridates, e.g., GB in situ by mixing a phosphorous ester in an aprotic solvent with a solution of tetraethylammonium in the same solvent.

5 Claims, No Drawings

PROCESS FOR PREPARING ORGANOPHOSPHORUS AND ORGANOPHOSPHONO FLUORINES

DEDICATORY CLAUSE

The invention described herein may be manufactured, used, and licensed by or for the Government for governmental purposes without the payment to us of any royalty thereon.

DESCRIPTION OF THE INVENTION

Our invention relates to a method of preparing anticholinesterase organophosphorus-fluorine and organophosphonofluoridate compounds in situ through the step of mixing a phosphorus ester in an aprotic solvent, such as acetonitrile, with a solution of tetraethylammonium fluoride.

The invention further relates to a method of preparing a toxic agent in situ for use in training exercises and in testing agent alarm operations in the field.

Applicants' invention has succeeded in satisfying a long felt need in the toxic agent field for an in situ method for extremely rapid preparation of very low concentrations of anticholinesterase organophosphorus-fluorine compounds. The instant invention further satisfies the safety needs for using only very small quantities of reactant phosphorous ester, which often itself possesses some anticholinesterase activity.

It is an object of this invention to provide an improved method of preparing toxic anticholinesterase organophosphorus-fluorine compounds in situ by mixing a phosphorus ester in an aprotic solvent with a solution of tetraethylammonium fluoride in the solvent.

Another object of this invention is to provide an extremely rapid process for preparing very small quantities of toxic organophosphorus-fluorine compounds in solution for use in training exercises, field testing of agent alarms, and pest control.

These and other objects of this invention will be apparent to those skilled in the art from the following description of the invention.

According to the invention, toxic anticholinesterase organophosphorus-fluorine and organophosphonofluorine compounds are prepared in situ by mixing the appropriate corresponding phosphorus ester in an aprotic solvent with a solution of tetraethylammonium fluoride in the same aprotic solvent.

Thus, for example, the toxic agent isopropyl methylphosphonofluoridate, i.e., GB can be prepared in situ by mixing m-nitrophenyl isopropyl methylphosphonate in an aprotic solvent, such as acetonitrile, with a solution of tetraethylammonium fluoride in acetonitrile.

In the above example for preparing methylphosphonofluoridate, the phosphorus ester used can be selected from corresponding esters which are less hazardous to handle, such as the quarternary ammonium salts.

Other toxic organophosphono-fluorine and organophosphorous-fluorine compounds such as pinacolyl methylphosphonofluoridate (GD), cyclohexyl methylphosphonofluoridate (GF), and diisopropyl phosphorofluoridate (DFP) can be synthesized by the instant process by substitution of the appropriate phosphorus ester.

Thus, the ester m-nitrophenyl diisopropyl phosphate can be used in the instant process to prepare the toxic agent diisopropyl phosphorofluoridate (DFP).

The process of this invention can be best shown by the following illustrative example of applicants' preferred method of preparing isopropyl methylphosphonofluoridate (GB):

EXAMPLE

To a 10 ml. of an acetonitrile solution containing 0.155 mg of m-nitrophenyl isopropyl methylphosphonate is added 50 ml. of acetonitrile solution containing 25 ± 5 mg. of tetraethylammonium fluoride. The two solutions were mixed well, allowed to sit for 1 minute at room temperature. The product solution contains ca 1.4 mg. GB/ml. or $10^{-5}$M.

In the process of this invention, the reaction conditions, e.g., concentrations, solvents and temperature can be varied to produce the organophosphorus-fluorine agent at different rates and in different quantities. The reaction conditions can thus be adjusted so as to use only very small stoichiometric quantities of the reactant ester, which is itself anticholinesterase active, and thereby reduce safety hazards in production.

The production of this invention can further include the step of sparging the solution to give off the toxic vapors in known quantities.

The process of this invention can be used to prepare a low concentration solution of anticholinesterase organophosphorus-fluorine and organophosphonofluorine compounds for training operations and for checking analytical precedures and equipment, such as agent alarms in the field. The process of this invention has further utility for producing a toxic solution, under controlled conditions, for use in pest control.

Applicants having disclosed their invention, obvious modifications of the invention will be apparent to those skilled in the related chemical agent art. Applicants therefore desire to be limited only by the scope of the appended claims.

We claim:

1. A process for preparing toxic organophosphorus-fluorine and organophosphono-fluorine compounds in situ comprising the step of mixing a phosphorus ester selected to produce a corresponding organophosphorus-fluoridate, in an aprotic solvent with a solution of tetraethylammonium fluoride in said solvent to produce a low concentration solution of anticholinesterase active organophosphorus-fluoridate.

2. The process of claim 1 wherein the phosphorus ester is selected to produce a corresponding organophosphono-fluorine compound of the class of toxic agents known as G agents.

3. The process of claim 2 wherein the phosphorus ester is m-nitrophenyl isopropyl methylphosphonate and the resultant toxic agent is isopropyl methylphosphonofluoridate (GB).

4. The process of claim 1 wherein the aprotic solvent is acetonitrile.

5. The process of claim 1 wherein the ester used is diisopropyl phosphate and the resultant toxic agent is diisopropyl phosphorofluoridate (DFP).

* * * * *